(12) United States Patent
Dewey et al.

(10) Patent No.: US 12,011,362 B2
(45) Date of Patent: Jun. 18, 2024

(54) BREAKAWAY ENDPLATE PORTIONS FOR IMPLANT REVISION

(71) Applicant: Warsaw Orthopedic, Inc., Warsaw, IN (US)

(72) Inventors: Jonathan M. Dewey, Memphis, TN (US); Julien J. Prevost, Memphis, TN (US); Richard A. Hynes, Melbourne Beach, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 315 days.

(21) Appl. No.: 17/394,715

(22) Filed: Aug. 5, 2021

(65) Prior Publication Data

US 2023/0039330 A1    Feb. 9, 2023

(51) Int. Cl.
| | | |
|---|---|---|
| *A61F 2/44* | (2006.01) | |
| *A61F 2/30* | (2006.01) | |
| *B05D 1/32* | (2006.01) | |
| *B05D 7/00* | (2006.01) | |
| *B33Y 80/00* | (2015.01) | |

(52) U.S. Cl.
CPC ........ *A61F 2/4455* (2013.01); *A61F 2/30771* (2013.01); *A61F 2/3094* (2013.01); *B05D 1/322* (2013.01); *B05D 7/50* (2013.01); *A61F 2002/3069* (2013.01); *B33Y 80/00* (2014.12)

(58) Field of Classification Search
CPC .. A61F 2/44; A61F 2/4455; A61F 2/30; A61F 2/3094; A61F 2/30771; B05D 7/00; B05D 7/50; B05D 1/32; B05D 1/322
See application file for complete search history.

(56) References Cited

U.S. PATENT DOCUMENTS

| | | |
|---|---|---|
| 5,895,428 A | 4/1999 | Berry |
| 6,517,580 B1 | 2/2003 | Ramadan et al. |
| 6,682,563 B2 | 1/2004 | Scharf |
| 6,726,720 B2 | 4/2004 | Ross et al. |
| 7,618,459 B2 | 11/2009 | Justin et al. |
| 7,621,956 B2 | 11/2009 | Paul et al. |
| 7,794,465 B2 | 9/2010 | Marik et al. |
| 8,632,594 B2 | 1/2014 | Williams et al. |
| 8,734,519 B2 | 5/2014 | de Villiers et al. |
| 9,248,028 B2 | 2/2016 | Gamache |
| 9,770,339 B2 | 9/2017 | Greenhalgh et al. |
| 10,786,364 B2 | 9/2020 | Davenport et al. |
| 2011/0190888 A1* | 8/2011 | Bertele .................. A61F 2/447 623/17.11 |
| 2018/0092754 A1* | 4/2018 | Jang ...................... A61F 2/4455 |

OTHER PUBLICATIONS

Frisch, Richard F., et al., "Clinical and radiograph analysis of expandable versus static lateral lumbar interbody fusion devices with two-year follow-up," Journal of Spine Surgery 2018;4(1), Mar. 1, 2018, pp. 62-71.

* cited by examiner

*Primary Examiner* — Christopher J Beccia
(74) *Attorney, Agent, or Firm* — Fletcher Yoder, P.C.

(57) ABSTRACT

An interbody spinal cage comprising: a body portion comprising a superior side, an inferior side and at least one lateral side connecting the superior side and the inferior side; and at least one endplate portion coupled to the superior side or the inferior side of the body portion, the at least one endplate portion comprising a unibody structure and operable to be fixedly coupled to an anatomical structure of a patient and decoupled from the superior side or the inferior side of the body portion.

12 Claims, 14 Drawing Sheets

BREAKAWAY ENDPLATE PORTIONS FOR IMPLANT REVISION

FIELD

The present technology is related generally to interbody devices having breakaway endplates for implant revision. Other aspects are also described and claimed.

BACKGROUND

The spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the vertebrae and discs may become diseased or infected, develop deformities such as tears and cracks, or simply lose structural integrity, for example bulge or flatten. These impaired vertebrae and discs can result in a lack of proper biomechanical support, and are often associated with chronic back pain.

Several surgical techniques have been developed to address spinal defects, such as vertebral or disc degeneration, deformity, or both. Spinal fusion has become a recognized surgical procedure for mitigating back and neck pain by restoring biomechanical and anatomical integrity to the spine. Spinal fusion techniques may involve the removal, or partial removal, of at least one intervertebral disc and preparation of the disc space for receiving an implant by shaping the exposed vertebral endplates. Such techniques may also involve removing all or part of the vertebral body located proximate the disc. An interbody device is then inserted.

An interbody device such as a spinal implant may be inserted during a spinal fixation procedure using an anterior, lateral, posterior, or transverse spinal approach. A discectomy may be performed to remove or partially remove a defective or damaged intervertebral disc. The discectomy may create a space for one or more spinal implants. The amount of removed disc material may correspond to the size and type of the spinal implant or spinal implants to be inserted. A corpectomy is a surgical procedure that involves removing all or part of the vertebral body (in Latin called a "corpus vertebrae," hence the name corpectomy), usually as a way to decompress the spinal cord and nerves. A corpectomy is often performed in association with some form of discectomy.

Several interbody implant systems have been introduced to facilitate interbody fusion. One such system includes a cage implant which is generally shaped to mimic the anatomical contour of the vertebral body. Once the cage implant is in place between the vertebrae, often the surrounding bone grows into the surface of the cage. Revision spine surgery, in which the implant is removed and replaced with a new one, can therefore be difficult and require excising part of the surrounding vertebrae.

SUMMARY

An aspect of the disclosure is directed to an interbody device having endplate portions that breakaway during revision spine surgery so the implant can be revised without removal of surrounding bone. The interbody device could be an expandable, multi-piece or static interbody device such as an implant or cage used to replace a damaged spinal disk during a spinal fusion procedure. In some aspects, the interbody device may be a unibody device with breakaway endplates added to a superior or inferior side of the unibody device, or formed into the superior or inferior surfaces. For example, the unibody device could be a cage implant with endplates formed on the superior side and the inferior side that will remain attached to the adjacent vertebrae upon removal of the cage during revision surgery. In some aspects, the endplate may be separate structures that are formed, and then attached to the superior and/or inferior sides of the cage at fixation points that allow the endplates to separate from the cage and remain attached to the adjacent vertebrae when the cage is removed during a revision surgery. In other aspects, the endplate may be a surface coating that is applied to the superior and/or inferior sides of the cage in such a manner that the coating will breakaway from the cage and remain attached to the adjacent vertebrae during removal of the cage. Having endplates that can breakaway from the implant as disclosed herein will reduce the amount of disruption to the surrounding vertebrae and ease removal of the implant during a revision surgery. In addition, in some aspects, the endplate may be complimentary to the new implant inserted during the revision surgery such that it can help to secure the new implant in place between the adjacent vertebrae.

In one aspect, the present disclosure includes an interbody spinal cage including a body portion comprising a superior side, an inferior side and at least one lateral side connecting the superior side and the inferior side; and at least one endplate portion coupled to the superior side or the inferior side of the body portion, the at least one endplate portion comprising a unibody structure and operable to be fixedly coupled to an anatomical structure of a patient and decoupled from the superior side or the inferior side of the body portion. In some aspects, the endplate portion is operable to be decoupled from the superior side or the inferior side upon application of a prying force between the endplate portion and the anatomical structure. In other aspects, the endplate portion is coupled to the superior side or the inferior side by at least one fixation point near an anterior edge of the body portion. In still further aspects, the endplate portion is coupled to the superior side or the inferior side by a number of fixation points around a perimeter of the body portion. In some aspects, the endplate portion includes a coating formed on the superior side or the inferior side of the body portion. In addition, the endplate portion may include a number of material layers applied to the superior side or the inferior side of the body portion. The endplate portion may include a mesh. In some aspects, at least one gap is formed between the endplate portion and the superior side or the inferior side to facilitate decoupling of the endplate portion from the body portion. In some aspects, at least one slot leading into the at least one gap is formed in the body portion.

In another aspect, an interbody spinal implant is provided including a body portion comprising a superior side, an inferior side and at least one lateral side connecting the superior side and the inferior side; and at least one endplate coating formed on the superior side or the inferior side of the body portion, the at least one endplate coating operable to be fixedly coupled to an anatomical structure of a patient and decoupled from the body portion. The endplate coating may include a single layer of endplate material formed on the superior side and the inferior side of the body portion. The endplate coating may include a first layer of endplate material formed on the superior side or the inferior side of the body portion, and a second layer of endplate material formed on the first layer of endplate material. In some aspects, the second layer of endplate material may remain fixedly coupled to the anatomical structure and is operable to be decoupled from the first layer of endplate material to decouple the endplate coating from the body portion.

In some aspects, a method of manufacturing an interbody spinal cage may include providing an interbody spinal cage having a superior side, an inferior side, and an anterior side, a posterior side and a lateral side connecting the superior side and the inferior side; and processing the interbody spinal cage to form an endplate portion at the superior side or the inferior side, and wherein the endplate portion is operable to remain fixedly attached to an anatomical structure of a patient when the interbody spinal cage is removed from the patient. In some aspects, processing the interbody spinal cage to form the endplate portion may include forming the endplate portion as a single unibody structure; and forming at least one fixation point between the endplate portion and the interbody spinal cage to couple the endplate portion to the body portion at the fixation point. In some aspects, forming the at least one fixation point includes forming a tack weld between the endplate coating and the body portion. In some aspects, the at least one fixation point is located at an anterior portion of the interbody spinal cage. In some aspects, the endplate portion is an endplate coating, and processing the interbody spinal cage to form the endplate coating comprises a plasma coating process, a hydroxyapatite coating process or three dimensional printing. In some aspects, processing further includes, prior to applying multiple layers of the coating material, masking portions of the superior side or the inferior side; and after applying multiple layers of the coating material, removing the masking to form gaps between the endplate coating and the interbody spinal cage. In some aspects, processing the interbody spinal cage to form the endplate portion includes forming at least one channel through the anterior side, the posterior side or the lateral side of the interbody cage, and wherein the at least one channel run parallel to the superior side and the inferior side; and forming at least one slot at the end of the at least one channel.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect in this disclosure are not necessarily to the same aspect, and they mean at least one.

DETAILED DESCRIPTION

In this section we shall explain several preferred aspects of the disclosure with reference to the appended drawings. Whenever the shapes, relative positions and other aspects of the parts described in the aspects are not clearly defined, the scope of the invention is not limited only to the parts shown, which are meant merely for the purpose of illustration. Also, while numerous details are set forth, it is understood that some aspects of the invention may be practiced without these details. In other instances, well-known structures and techniques have not been shown in detail so as not to obscure the understanding of this description.

The terminology used herein is for the purpose of describing particular aspects only and is not intended to be limiting of the disclosure. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Figure 1:
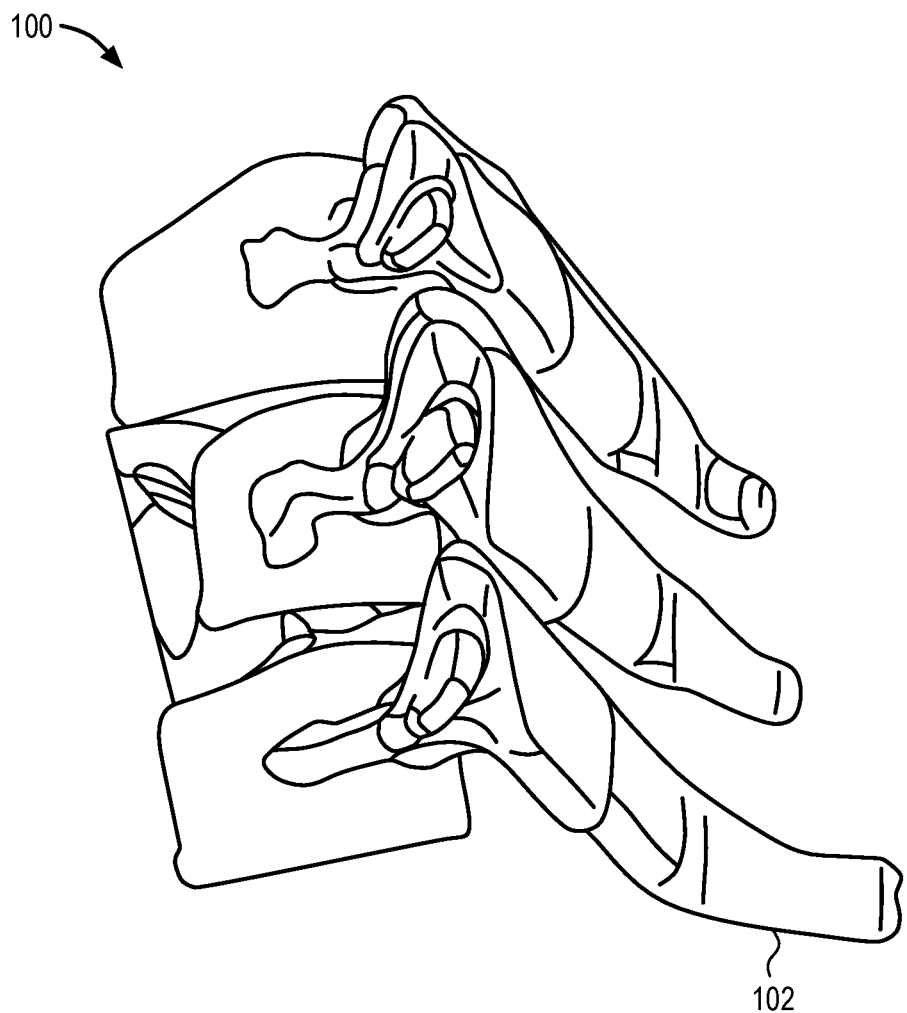
FIG. 1 shows a representation of a functional spinal unit.
Figure 2A:
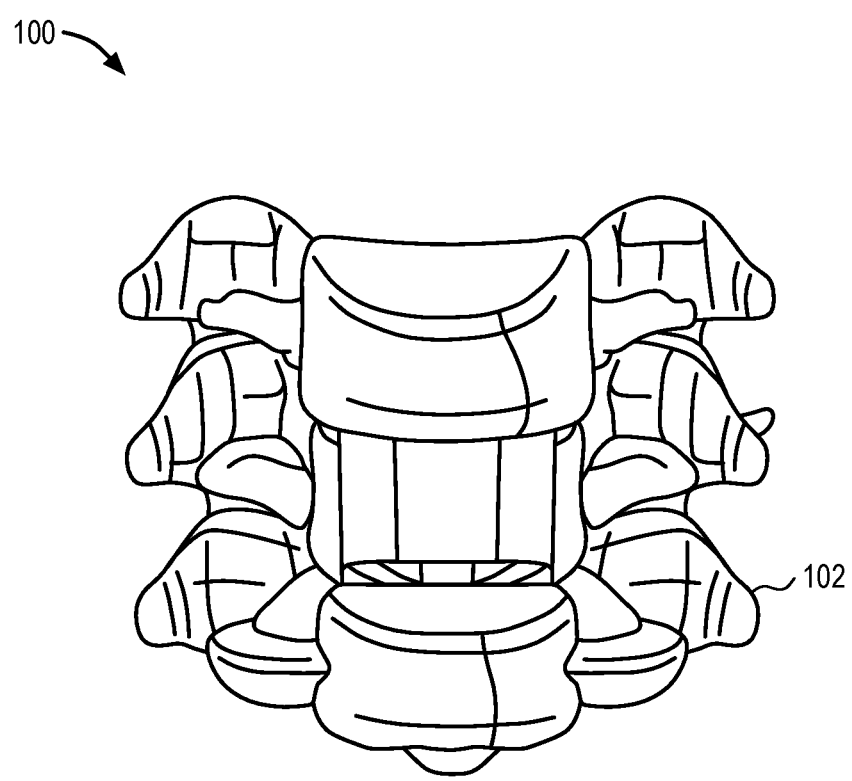
FIG. 2A shows an anterior view of a partial corpectomy of a vertebra.
Figure 2B:
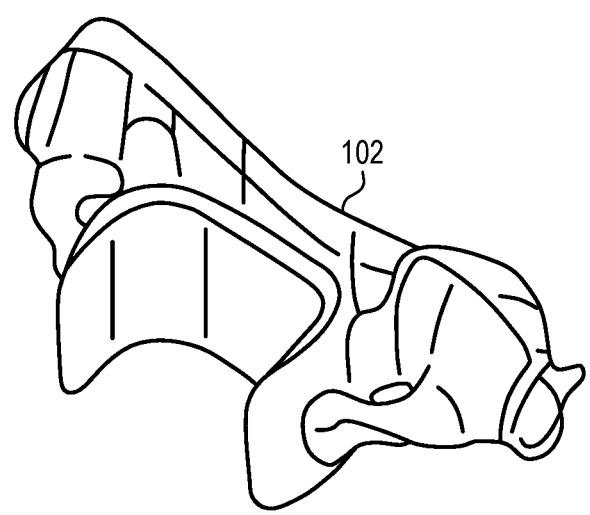
FIG. 2B shows a perspective view of a partial corpectomy of a vertebra with a portion of the vertebral endplate removed.
Figure 2C:
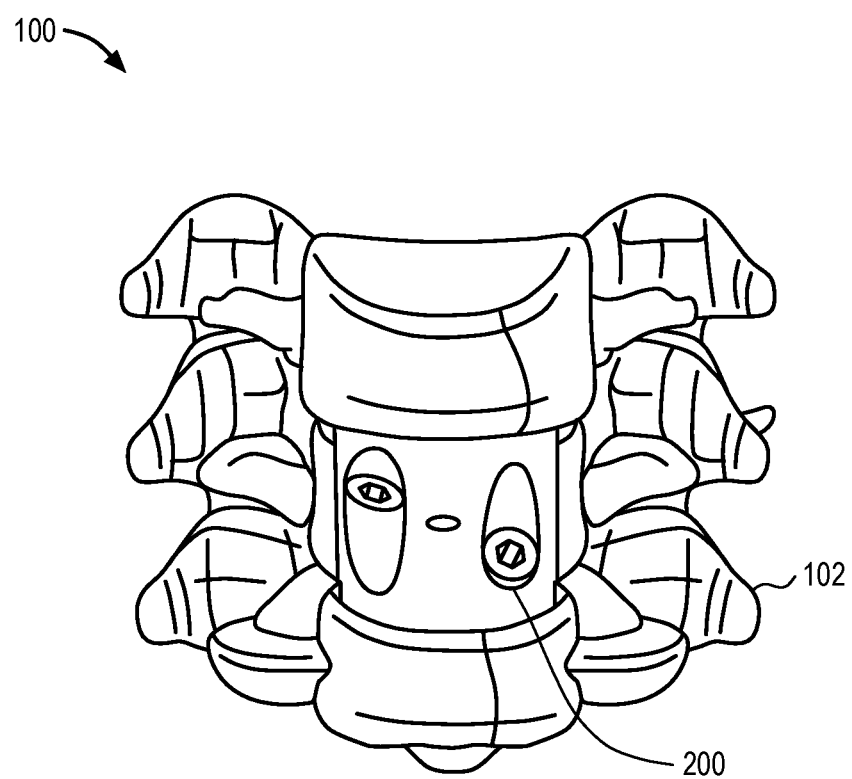
FIG. 2C shows an implant inserted into the channel of the vertebra.

Referring now to FIG. 1, in which like reference numbers refer to like elements throughout the various figures that comprise the drawing, implants in accordance with certain aspects of the disclosure stand in the place of at least a portion of at least one vertebrae 102, including in the place of a functional spinal unit 100 which is illustrated in FIG. 1. The implants are preferably used in accordance with surgical procedures, as illustrated in FIG. 2A and FIG. 2B, that retain some portion of a vertebrae 102. FIG. 2A shows an anterior view of a partial corpectomy of a vertebra 102, and FIG. 2B shows a perspective view of a partial corpectomy of a vertebra 102 with a portion of the vertebral endplate removed. Such surgical procedures allow the implant to be seated in place of the removed portion and contact the extant bone, while the top and bottom surfaces of the implant contact the inferior and superior surfaces of adjacent vertebrae 102, including vertebral endplate bone. FIG. 2C shows an implant 200 inserted into the channel of the vertebra 102.

Implants in accordance with certain aspects of the disclosure may be made of a durable material such as metals, hut can also be made of other durable materials such as, but not limited to, plastic, polymeric, silicone, ceramic, bone, and composites of any such materials. Suitable polymers include polyether ether ketone (PEEK) and ultra-high molecular weight polyethylene (UHMWPE), as well as urethane dimethacrylate (DUDMA)/tri-ethylene glycol dimethacrylate (TEDGMA) blended resin. Certain aspects of the disclosure may be comprised of a biocompatible, polymeric matrix reinforced with bioactive fillers, fibers, or both. Certain aspects of the disclosure may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also include any number of pure metals, metal alloys, or both. Titanium and its alloys are generally preferred for certain embodiments of the invention due to their acceptable, and desirable, strength and biocompatibility. Suitable metals may include titanium, an alloy of titanium such as an aluminum and vanadium alloy, of titanium (e.g., 6-4), a nickel alloy of titanium such as nitinol, a cobalt chromium alloy, surgical grade steel, stainless steel, or stainless steel alloy. In this manner, certain aspects of the interbody spinal implant disclosed herein may have improved structural integrity and may better resist fracture during implantation by impact. Interbody spinal implants, as now taught, may therefore be used as a distractor or trial implant during implantation.

The disclosure relates to an implant having breakaway (e.g., removable) endplates that breakaway from the implant and remain attached to the adjacent vertebrae during implant revision surgery. In some aspects, the breakaway endplates may be formed on the implant, or as part of the implant, during implant manufacture (e.g., prior to a surgical procedure). In other aspects, the breakaway endplate may be provided as a separate component to the implant (e.g., assembled with the implant by the surgeon during a surgical procedure). The implant may be especially suited for placement between adjacent human vertebral bodies. The implants may be used in procedures such as Anterior Lumbar Interbody Fusion (ALIF), Posterior Lumbar interbody Fusion (PLIF), Transforaminal Lumbar Interbody Fusion (TLIF), and cervical fusion. During revision surgery, an anterior or posterior approach may be used to insert a tool between the implant and the adjacent vertebrae. The tool is then manipulated to separate the implant from the adjacent vertebrae. Once separated, the old implant is removed and a new implant can be inserted. As previously discussed, because the bone is often attached to the implant, portions of the vertebrae bone may also need to be removed along with the implant. The implant disclosed herein requires less, or possibly no, bone removal by having endplates which will remain attached to the bone and breakaway, or otherwise become decoupled, from the implant during removal of the implant. Since the endplate remains attached to the vertebrae, none of the vertebrae bone needs to be removed, or otherwise disturbed, during the revision surgery. In addition, in some aspects, the endplate may be complimentary to the new implant placed between the vertebrae. In this aspect, the new implant can be easily inserted and attached to the endplate already in place. The endplate from the old implant therefore serves as the endplate for the new implant. In still further aspects, the endplate may also be configured to breakaway from the new implant as previously discussed, in case further revision surgery is necessary.

Representatively, FIG. 3, FIG. 4, FIG. 5 and FIG. 6 illustrate schematic cross-sectional side views of a representative implant having breakaway endplates. In one aspect, an implant 302 having endplates 304 and 306 is shown inserted between two adjacent vertebrae 102. Representatively, implant 302 may, for example, be made up of a body portion having a top or superior side 302A, a bottom or inferior side 302B, anterior side 302C and posterior side 302D. Representatively, in one aspect, implant 302 may be an expandable or adjustable corpectomy cage. In some aspects, the top or superior side 302A may be considered or referred to herein as a superior side or surface of the implant because it faces toward the head end of the body when inserted in the body/coronally. The bottom or inferior side 302B may be considered or referred to herein as an inferior side or surface of the implant because it faces away from the head when inserted in the body. Endplate 304 may be attached to the top or superior side 302A and endplate 306 may be attached to the bottom or inferior side 302B. In this aspect, when implant 302 is inserted in the body, endplate 304 of implant 302 presses against an anatomical structure (e.g. vertebrae) of the patient and endplate 306 presses against an opposing anatomical structure of the patient. In some aspects, endplates 304, 306 may also be referred to herein as superior and/or inferior surfaces, respectively, of implant 302 since they essentially form the outermost bone contacting surfaces of implant 302. In still further aspects, endplates 304, 306 may be referred to herein as bone contacting surfaces since they contact the adjacent vertebrae bone once inserted. In some aspects, the bone contacting surfaces may further include surface features that promote bone growth on or in the surfaces. For example, raised features that have a macro-scale, micro-scale or nano-scale roughness may be formed on the bone contacting surfaces. Each roughness may comprise regular, irregular, or combinations of regular and irregular structural features in terms of the structural arrangement of the surface.

Figure 3:
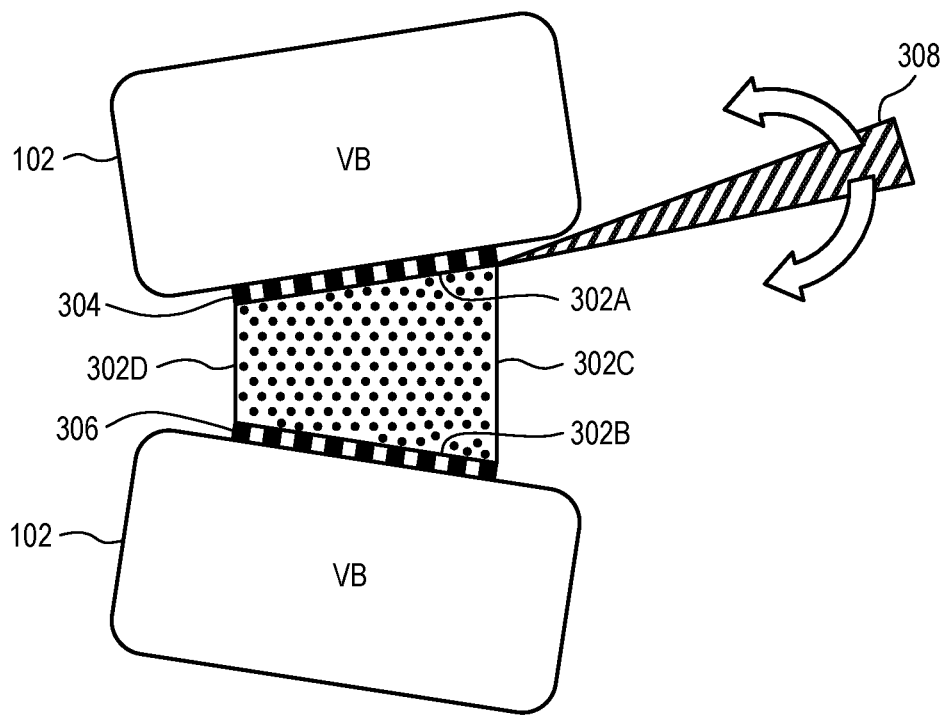
FIG. 3 shows a side cross-sectional view of one aspect of an interbody spinal implant.

As shown in FIG. 3, endplate 304 attaches the superior side 302A of implant 302 to the superior vertebrae 102. Similarly, endplate 306 attaches the inferior side 302B of implant 302 to the inferior vertebrae 102. In some aspects, each of endplates 304, 306 may be considered a unibody structure. The term "unibody" is intended to refer to a structure that is formed as a single and inseparable unit configured to attach to a side of implant 302. In this aspect, the entire portion of the endplate 304, 306 attached to superior side or inferior side 302A, 302B of implant 302 is also removed when endplate 304, 306 breaks away, or is otherwise decoupled from, implant 302. In other words, endplates 304, 306 do not have a separate endplate piece in the center that is removed from, or attached to, the rest of the endplate 304, 306 to couple or decouple endplates 304, 306 to/from implant 302. In this aspect, endplates 304, 306 may also be considered solid structures in that they are formed without any openings or hollow features, spaces or gaps therein. For example, in some aspects, endplates 304, 306 may cover the entire superior side or inferior side 302A, 302B to which they are coupled such that they form a solid, inseparable, upper most or lower most surface of implant 302.

In still further aspects, endplates 304, 306 may cover only a portion of the superior or inferior surfaces of the implant 302 such that only a portion is needed to break off, instead of having to break off the entire top surface. For example, in some aspects, endplates 304, 306 could be stripes that run from anterior to posterior dies, but not the full width between lateral sides, or have a horseshoe or donut shape with an exposed portion of implant 302 in the middle. In the case of only a partial covering of sides 302A-B, the sides 302A-B could be covered with or made of materials that repel bone growth such that, during the loosening of cage 302, the "naked" faces of implant 302 wouldn't need to be loosened from the bone. Also, the "naked" spots could be treated with bone growth factors such that, during removal, the implant 302 actually disrupts the endplate; in this way, the disrupted bone might be receptive to forming bone such that it would bond to a new implant, further securing the new implant to both the old endplates 304, 306 and the vertebrae.

During an implant revision surgery, tool 308 may be inserted between endplate 304 or endplate 306 and the adjacent vertebrae 102. In FIG. 3, tool 308 is shown inserted between endplate 304 and vertebrae 102 from the anterior side. Tool 308 may be, for example, a flat chisel or a cobb, a pointed pick or conically shaped tool, a specially designed tool for separating the two items, or other similar tool used for revision surgery that can be wedged in between the endplate 304 and implant 302 to break the endplate 304 away from the implant 302 during a revision surgery. For example, tool 308 may be moved up and down in a prying or pivoting motion, or even in a twisting motion as could be used with a flat tool, as illustrated by the arrow to separate endplate 304 from implant 302. Although not shown, a similar operation may be used to separate endplate 306 from implant 302. The attachment between endplates 304, 306 and the bone (e.g., vertebrae 102) may be stronger than the attachment between endplates 304, 306 and cage 302, but may be weaker than the main body 302, such that neither implant 302 or endplates 304, 306 break apart during this part of the procedure. In this aspect, the force from the tool 308 causes endplates 304, 306 to break away, or otherwise become decoupled, from the cage 302 while remaining attached to vertebrae 102.

Figure 4:
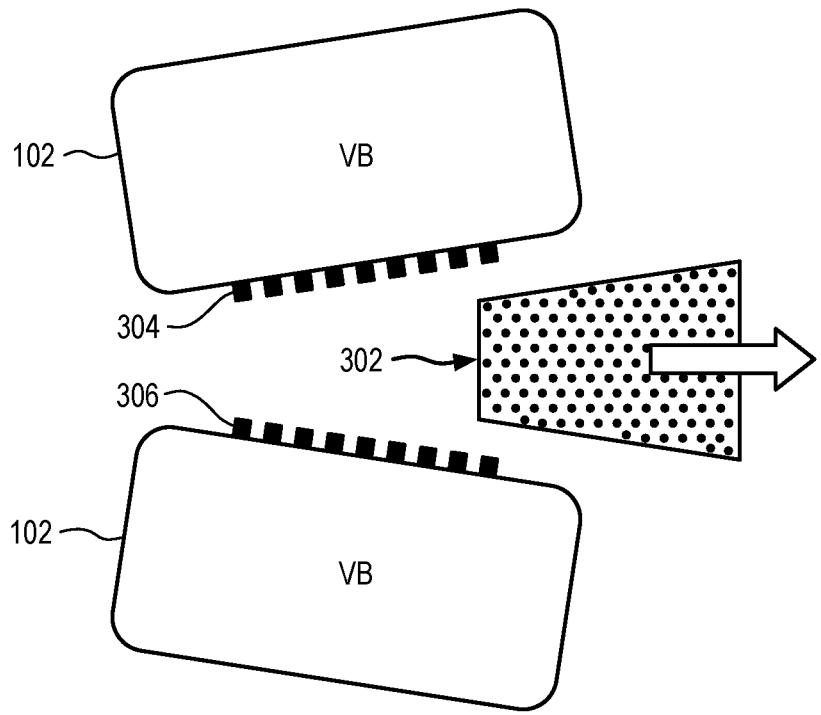
FIG. 4 shows a side cross-sectional view of another aspect of an interbody spinal implant.

Once the endplates 304, 306 are separated, or otherwise decoupled from implant 302, implant 302 can be removed in an anterior direction as illustrated by the arrow shown in FIG. 4. As can be further seen from FIG. 4, endplates 304, 306 remain attached to vertebrae 102. As can further be seen from FIG. 5, once the old implant 302 is removed, a new implant 302 can be inserted between the vertebrae 102 from the anterior side as shown by the arrow. Similar to the old implant, the new implant 302 may have a superior side and an inferior side that are complimentary to endplates 304, 306. The new implant 302 engages with, or otherwise attaches to, the endplates 304, 306 and is therefore held in place between vertebrae 102 by endplates 304, 306. In some aspects, endplates 304, 306 removably engage with the new implant 302 such that during a further revision surgery, the new implant 302 can be removed while the endplates 304, 306 remain in place to engage with a further new implant, if necessary.

Figure 5:
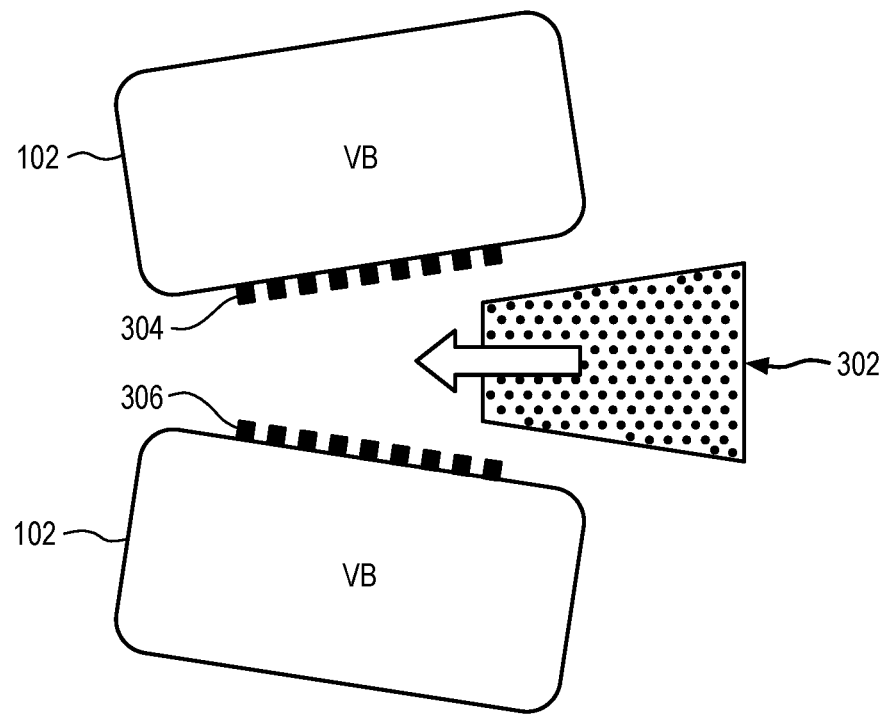
FIG. 5 shows a side cross-sectional view of another aspect of an interbody spinal implant.
Figure 6:
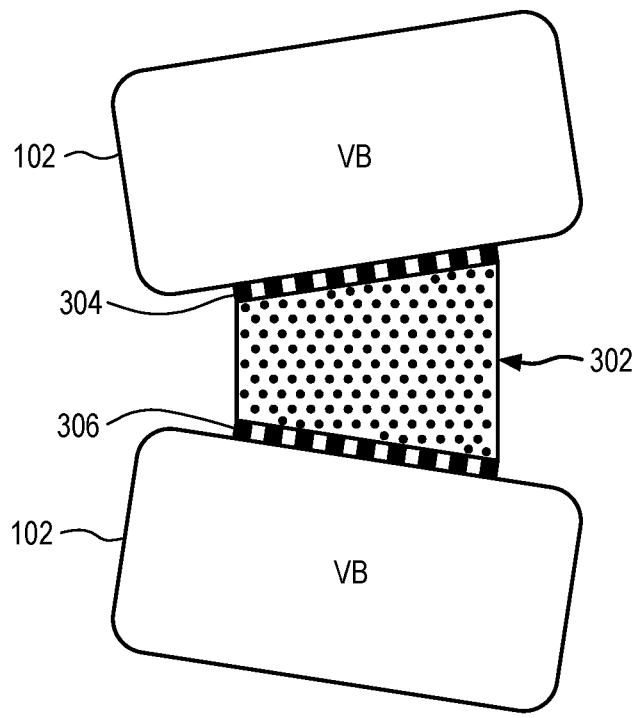
FIG. 6 shows a side cross-sectional view of another aspect of an interbody spinal implant.

Representatively, as shown in FIG. 5, the new implant 302 can be inserted between endplates 304, 306 still connected to the vertebrae 102, in the posterior direction as illustrated by the arrow. Once in place as shown in FIG. 6, the superior and inferior sides of the new implant 302 engage with the endplates 304, 306, respectively, so that new implant 302 is secured between vertebrae 102. Representatively, in some aspects, the surfaces of endplates 304, 306 facing new implant 302 may have structures that engage with complimentary structures on the superior and inferior sides of implant 302. The complimentary structures may include protrusions that engage with recesses, or some other complimentary structure configuration that allows endplates 304, 306 to engage with the new implant 302 as shown.

Figure 7:
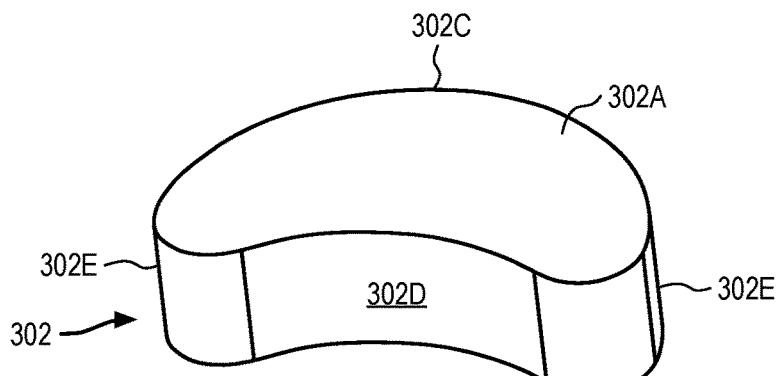
FIG. 7 shows a perspective view of another aspect of an interbody spinal implant.
Figure 8:
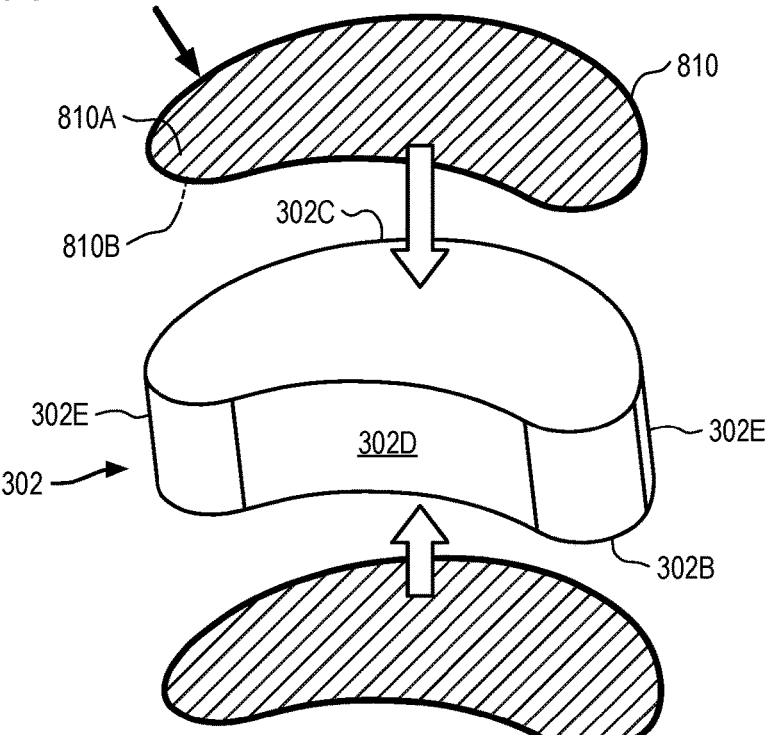
FIG. 8 shows a perspective view of another aspect of an interbody spinal implant.
Figure 9:
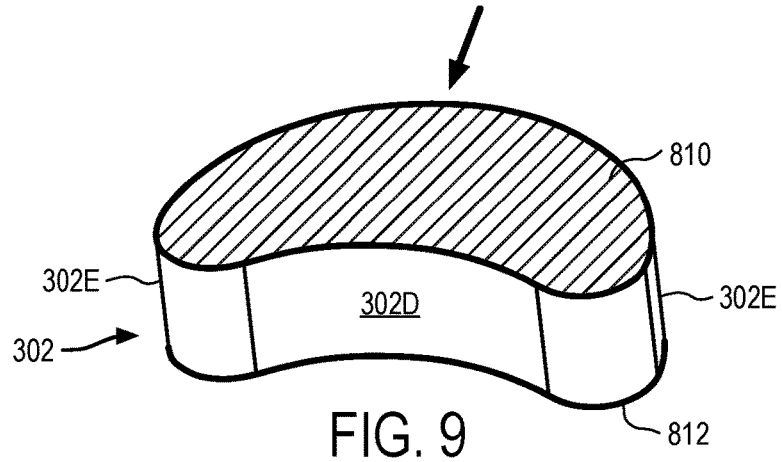
FIG. 9 shows a perspective view of another aspect of an interbody spinal implant.

Referring now to FIG. 7, FIG. 8 and FIG. 9, FIGS. 7-9 illustrate one exemplary implant having breakaway endplates, and a process for forming the same.

Representatively, FIG. 7 illustrates a perspective view of an implant 302, for example, a unibody cage implant. Implant 302 may also be referred to herein as an implant body, or the body portion of implant 302. Implant 302 may have superior side 302A, inferior side 302B, anterior side 302C, posterior side 302D and lateral sides 302E. As shown in FIG. 8, endplates 810, 812 may be separate components from the implant 302. Representatively, endplates 810, 812 could be substantially flat mesh like structures. In other aspects, endplates 810, 812 could be curved in one direction (uniconvex), as well as curved in multiple directions (biconvex), and could include unilateral features such as narrowed parts to ease insertion. Also, the endplates 810, 812 could be angled relative to one another such that the resulting cage is lordotic or kyphotic (e.g., like implant 302), and the implant could house a central (or multiple) cavities for filling with graft. Endplates 810, 812 may be considered unibody structures in that they do not have any separable pieces. Endplates 810, 812 may be formed by machining, stamping, forming, welding of layers or strands of material, 3D printing or grown with another additive process such as plasma coating or hydroxyapatite (HA) coating. Endplates 810, 812 may have a similar shape to that of the superior and inferior sides 302A, 302B, respectively, of implant 302. In this aspect, once formed, endplates 810, 812 may be positioned onto the superior and inferior sides 302A, 302B of implant 302 as shown by the arrows in FIG. 8. Endplates 810, 812 may be attached to the superior and inferior sides 302A, 302B as shown in FIG. 9. Endplates 810, 812 may be attached to implant 302 using any suitable attachment mechanism that allows for decoupling of endplates 810, 812 from implant 302 upon application of a sufficient force, as previously discussed.

Figure 10:
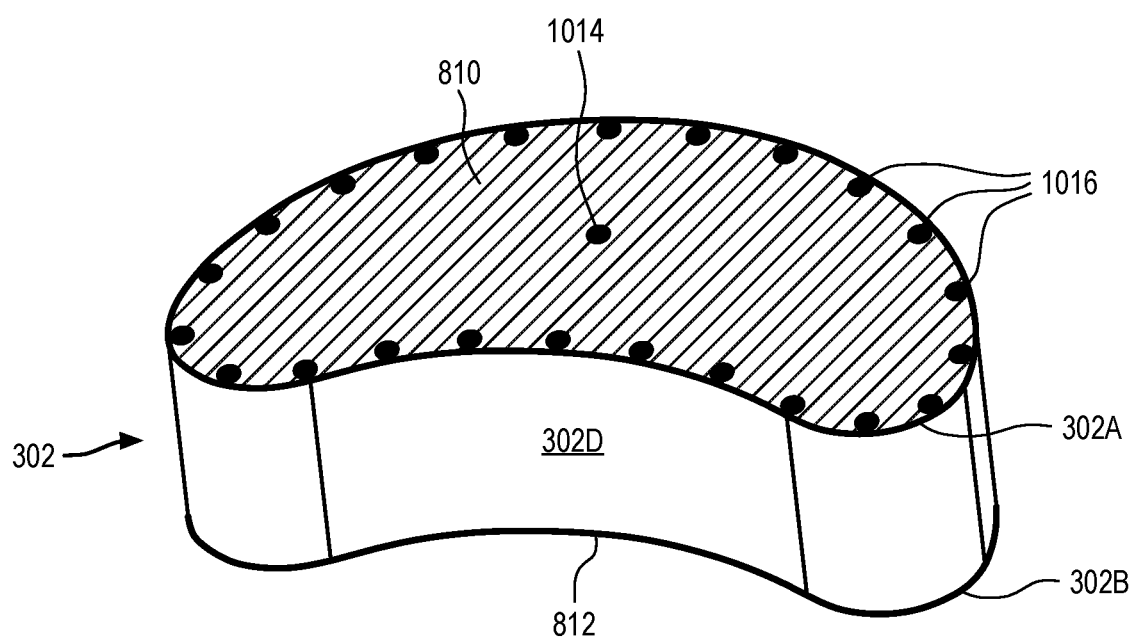
FIG. 10 shows a perspective view of another aspect of an interbody spinal implant.

One representative endplate attachment configuration is shown in FIG. 10. Representatively, endplates 810, 812 may be attached to the superior and inferior sides 302A, 302B of implant 302 at preselected fixation point(s) 1014 and/or 1016. The fixation point(s) could be located where insertion/manipulation forces would be highest, such as the leading edge of an impacted cage. Still further the fixation point(s) could be located in a position, location or area of the implant that is easily accessed for a revision surgery. Representatively, the fixation point could be a single fixation point 1014 at a center of implant 302. In addition, or alternatively, the fixation point could include any number of fixation points 1016 positioned around a perimeter of implant 302. For example, in the case of a TLIF cage implant 302, the implant 302 could have fixation points 1014, 1016 located primarily near the anterior side 302C of implant 302. In this aspect, as the implant 302 is impacted from posterior to anterior, the anterior fixation prevents the endplates 810, 812 from "peeling up" or separating. TLIF cage implants are often removed anteriorly, therefore the fixation points near the anterior side 302C could be easily accessed by the tool to separate the implant from the endplates 810, 812 and therefore ease removal. The fixation points could be formed by any number of fixation techniques including, but not limited to, gluing, welding (either a laser beam, torch or arc (a gun) welding, or resistance, electrode or ultrasonic welding), fasteners, complimentary surface structures/detents, press fit posts, or the like. Representatively, a tack weld (e.g., a small and/or temporary weld) could be formed at one or more of the desired fixation points. In other aspects, a continuous bead of weld could be formed around the perimeter of the superior and inferior sides 302A, 302B of the implant 302. The endplates 810, 812 could then be placed on the fixation points to secure the endplates 810, 812 to superior and inferior sides 302A, 302B as shown in FIG. 10.

Figure 11:
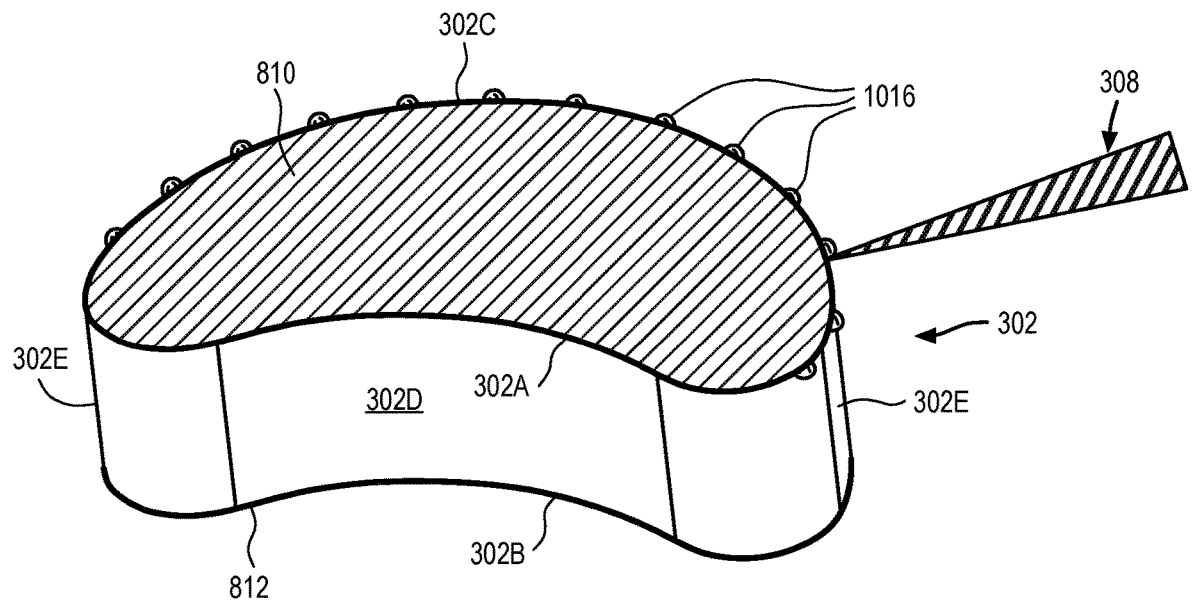
FIG. 11 shows a perspective view of another aspect of an interbody spinal implant.
Figure 12:
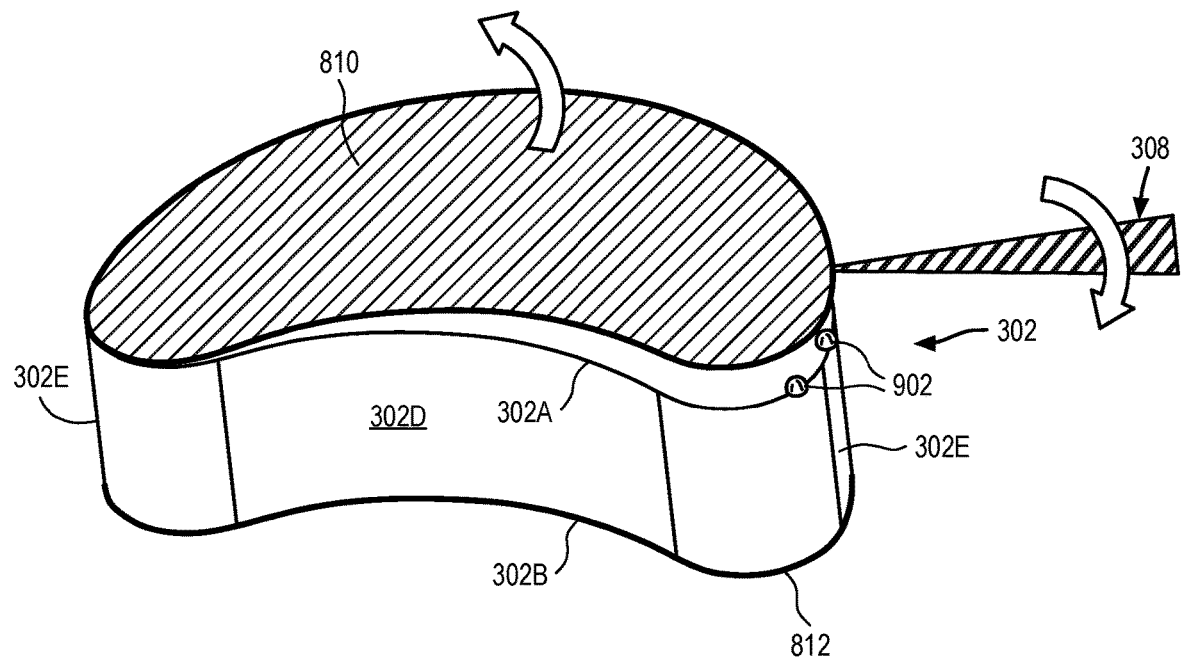
FIG. 12 shows a perspective view of another aspect of an interbody spinal implant.

FIG. 11 and FIG. 12 illustrate one representative implant having fixation points formed by any of the previous processing operations. Representatively, FIG. 11 illustrates implant 302 having fixation points 1016 for the endplates 810, 812 located around the portion of the perimeter at the anterior side 302C of implant 302. The fixation points 1016 may be spot welds, and could be evenly spaced apart such that gaps are formed between each of fixation points 1016. To breakaway, or remove, endplates 810, 812 from implant 302, tool 308 is inserted into the gaps between fixation points 1016, and between endplates 810, 812 and the superior and/or inferior sides 302A, 302B of implant 302. The tool 308 could then be manipulated by the surgeon to break the fixation points 1016 (e.g., the weld spots) allowing for endplates 810, 812 to be pried away from implant 302 as shown in FIG. 12. For example, tool 308 could be manipulated to pull endplates 810, 812 away from implant 302, which in turn breaks the fixation points 1016. In addition, in some aspects, laser marks, grooves, undercuts or other features 902 could be formed in implant 302, near the fixation points 1016, to make the removal points easier to identify and/or the tool easier to insert. It should further be noted that even though fixation points 1014, 1016 may be used to attach endplates 810, 812 to implant 302, endplates 810, 812 themselves are still considered unibody or inseparable structures since the entire portion of the endplate structure attached to the implant is removed when endplates 810, 812 breakaway from implant 302.

Figure 13:
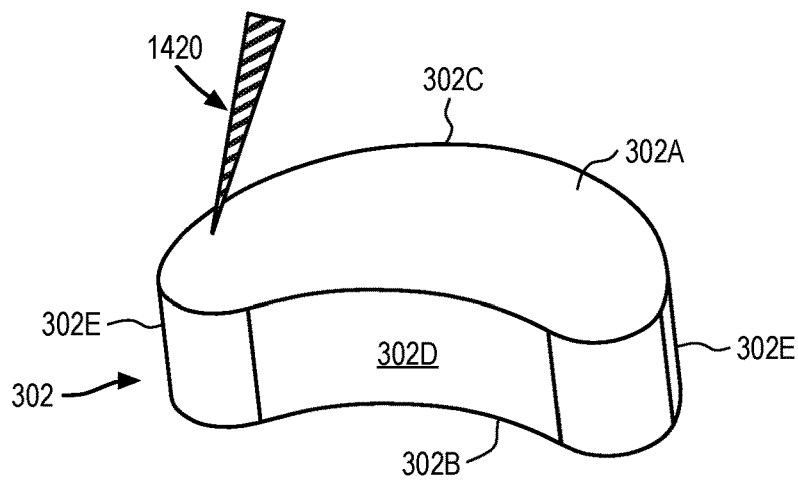
FIG. 13 shows a perspective view of another aspect of an interbody spinal implant.
Figure 14:
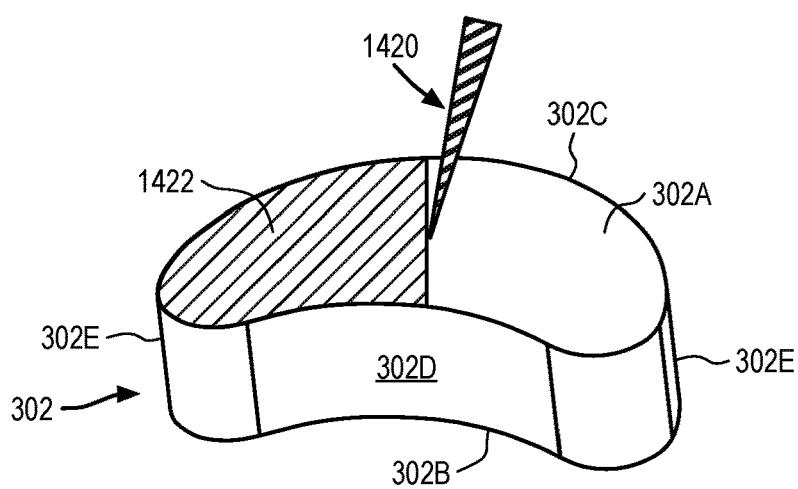
FIG. 14 shows a perspective view of another aspect of an interbody spinal implant.
Figure 15:
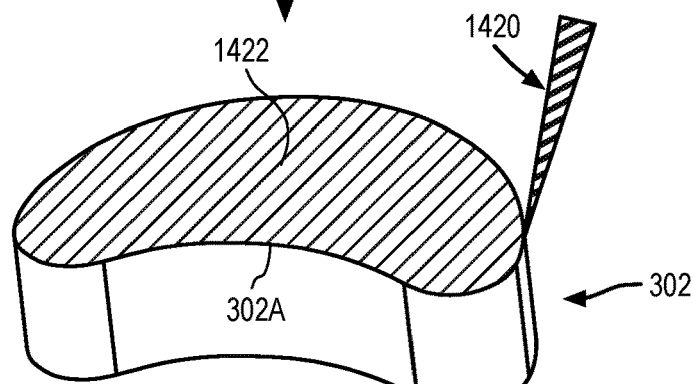
FIG. 15 shows a perspective view of another aspect of an interbody spinal implant.

FIG. 13, FIG. 14 and FIG. 15 illustrate another implant with endplate configuration, and processing operations for forming the same. Representatively, implant 302 is provided as shown in FIG. 13. Implant 302 may include superior side 302A, inferior side 302B, anterior side 302C and posterior side 302D connected by lateral sides 302E. In this configuration, the endplates are applied to, or otherwise formed on, the superior side 302A and/or inferior side 302B using a nozzle 1420. Representatively, nozzle 1420 could be used to apply an endplate material onto the superior side 302A and/or inferior side 302B through a subtractive manufacturing process, or through 3D printing or other additive material process, such as plasma coating or hydroxyapatite (HA) coating. As can be seen from FIG. 14 and FIG. 15, the endplate material (e.g., hydroxyapatite) is applied across the superior side 302A and/or inferior side 302B using the applicator or nozzle 1420. The nozzle 1420 may sweep across the desired side or surface to form a coating 1422. The coating 1422 may be a uniform coating or a non-uniform coating. FIG. 15 shows the completely coated implant in which coating 1422 may then serve as the endplates for the implant 302. The coating 1422 may therefore also be understood, or referred to herein, as the endplate of implant 302. In addition, the endplate formed by coating 1422 may be considered a unibody structure or unibody endplate since it is a single inseparable or molded piece.

Figure 16:
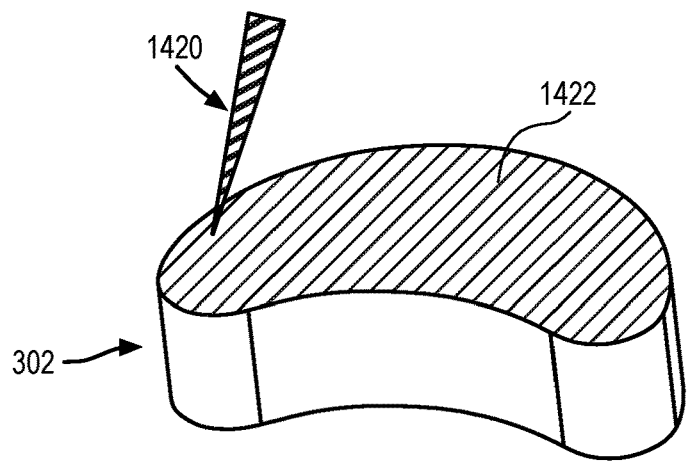
FIG. 16 shows a perspective view of another aspect of an interbody spinal implant.
Figure 17:
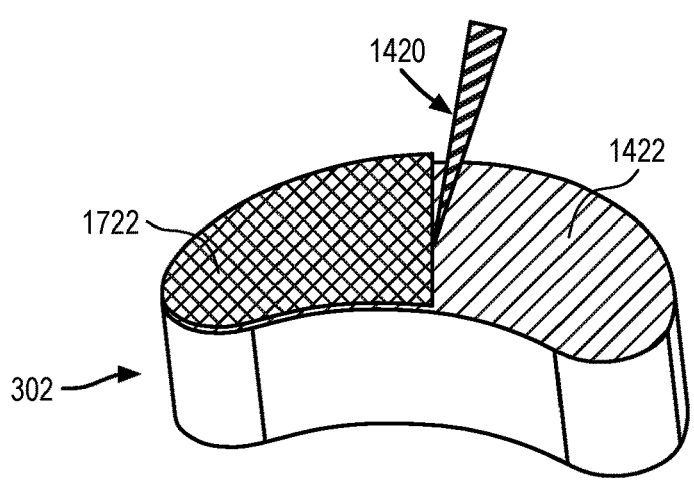
FIG. 17 shows a perspective view of another aspect of an interbody spinal implant.
Figure 18:
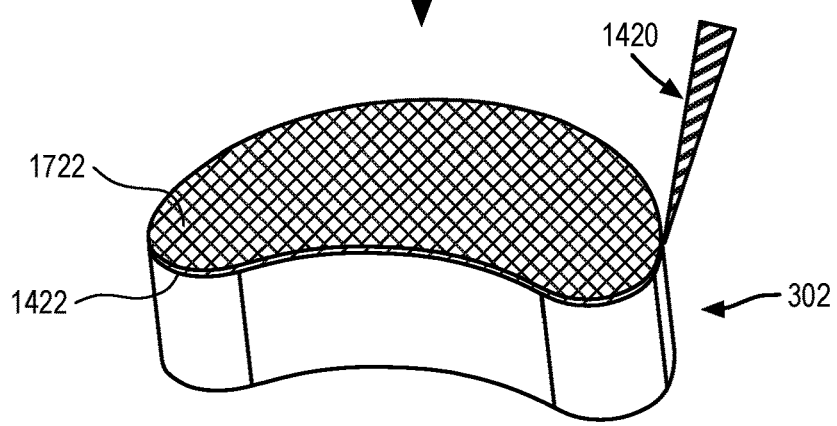
FIG. 18 shows a perspective view of another aspect of an interbody spinal implant.

FIG. 16, FIG. 17 and FIG. 18 illustrate a further aspect of an implant with endplates formed by a coating. Representatively, FIG. 16 illustrates the implant 302 with endplate coating 1422 previously discussed in reference to FIG. 15. As illustrated by FIG. 17, a second layer of coating 1722 may be applied over coating 1422 using nozzle 1420. The second layer of coating 1722 may be applied to increase the endplate thickness and/or increase separability between the implant and endplate. Similar to endplate coating 1422, endplate coating 1722 may be applied entirely across the implant 302 as shown in FIG. 18. In this aspect, the endplate (e.g., endplate 304, 306) may be considered formed by multiple layers of endplate material, for example, a first layer formed by coating 1422 and a second layer formed by coating 1722. The endplate material used to form coating 1722 may be the same or different than the endplate material used to form coating 1422. The endplate material and/or coatings may be selected to preferentially break from the implant 302 before breaking from the adjacent vertebrae.

In some aspects, the coating 1722 and/or coating 1422, alone or in combination, may have a thickness sufficient to form a single, coherent unified body so that it stays together when peeled from the cage. For example, a relatively thick HA layer (e.g., first layer coating 1422) could be deposited on the surface such that, as a shearing force is applied to the base of the coating, generally the boundary between the coating and implant could break free from each other. Representatively, in some aspects, coating 1722 and/or coating 1422, alone or in combination, may have a thickness of from about 0.3 millimeters to about 2 millimeters.

Figure 19:
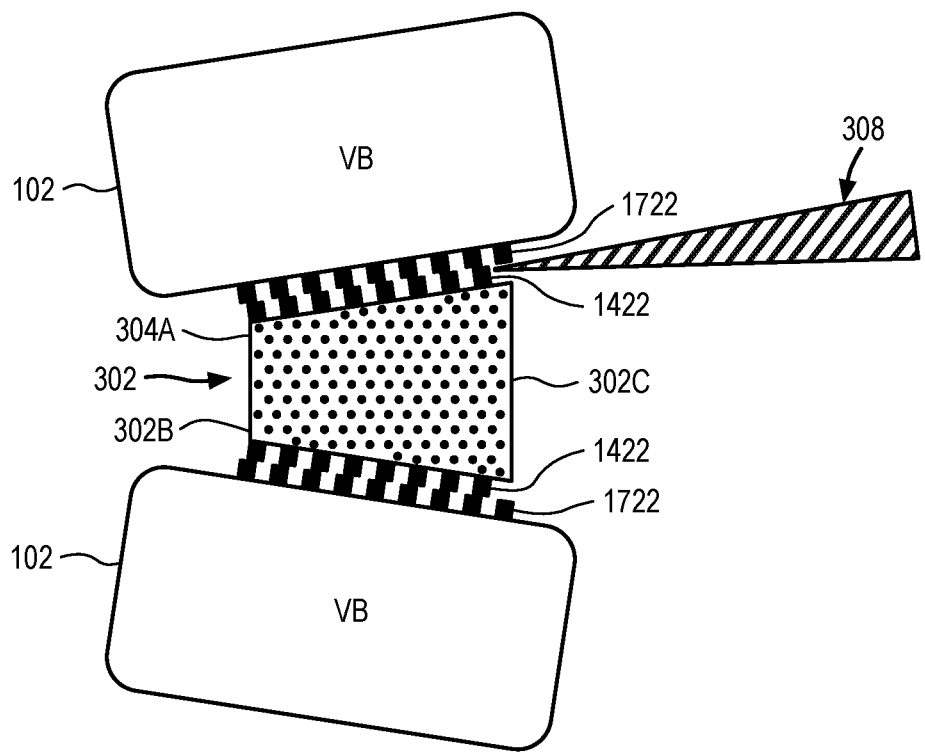
FIG. 19 shows a side cross-sectional view of another aspect of an interbody spinal implant.
Figure 20:
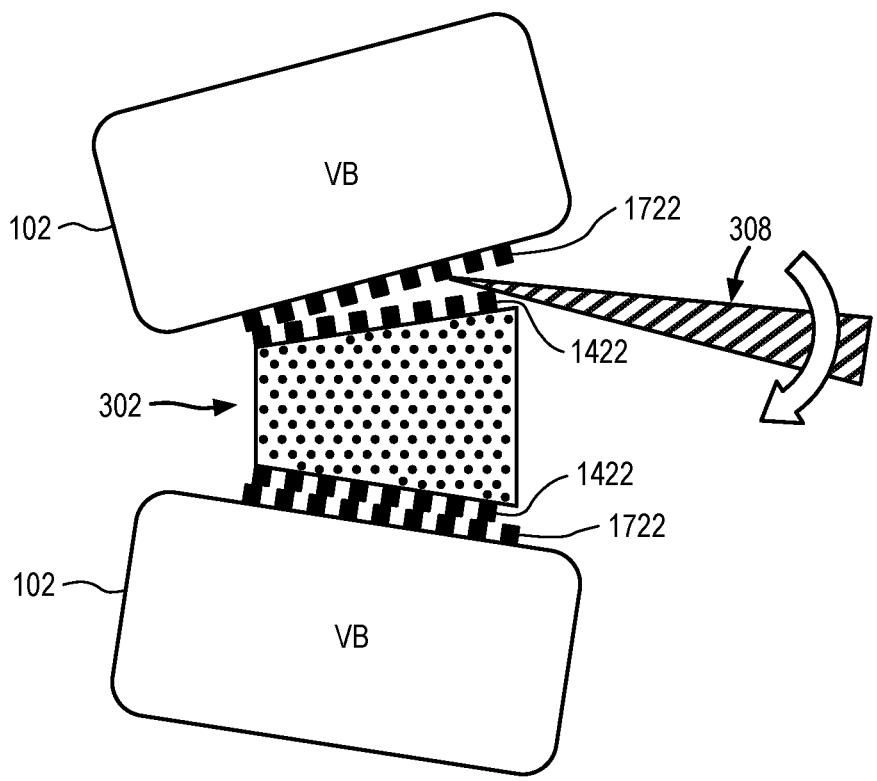
FIG. 20 shows a side cross-sectional view of another aspect of an interbody spinal implant.

Representatively, as illustrated by FIG. 19 and FIG. 20, to breakaway the endplate formed by coatings 1422/1722 from implant 302, the tool 308 may be inserted between the layer of coating 1422 and layer of coating 1722. The endplate materials for coatings 1422 and 1722 may be selected so that the layers of coating 1422 and 1722 will separate when force from the tool 308 is applied. Alternatively, in the case of a single endplate coating 1422 or 1722, the coating may be a thick endplate coating and the tool 308 inserted into the endplate coating, or between the endplate coating and the implant 302, to break the endplate coating away from implant 302. Representatively, as illustrated by FIG. 20, in one aspect, tool 308 may be inserted between endplate coating 1722 and endplate coating 1422. Tool 308 may then be manipulated by the surgeon to separate endplate coating 1722 from endplate coating 1422. Endplate coating 1722 may, in some aspects, remain attached to vertebrae 102 while endplate coating 1422 remains attached to implant 302. Once endplate coatings 1722 and 1422 are separated, implant 302 can be removed with the endplate coatings 1422 attached thereto. Endplate coatings 1722 attached to the vertebrae 102 may engage with a new implant inserted during a revision surgery. In other aspects, tool 308 is inserted between endplate coating 1422 and implant 302 such that both endplate coatings 1422 and 1722 breakaway from implant 302 and remain attached to vertebrae 102 when implant 302 is removed. It should further be understood that regardless of whether endplate coatings 1422, 1722 are separated or remain together (e.g., attached to the adjacent bone) during implant removal, the endplate formed by the coatings 1422, 1722 is still considered to have a unibody structure. In particular, the endplate is still considered to have a unibody structure since at least the portion of the endplate attached to the implant 302 (e.g., endplate coating 1422) does not include separable portions or structures, rather it is a single coating layer that is either entirely removed from, or remains entirely attached to, implant 302 during removal.

Figure 21:
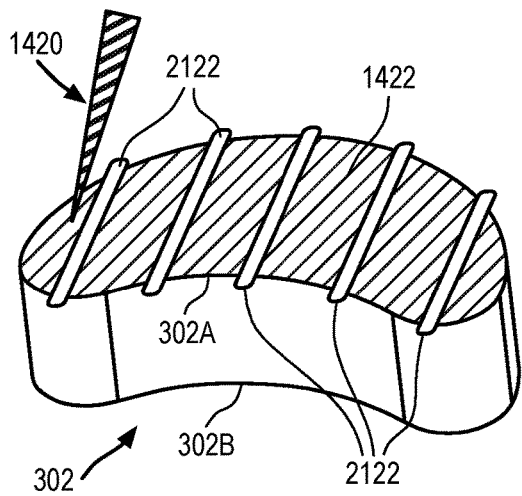
FIG. 21 shows a perspective view of another aspect of an interbody spinal implant.

FIG. 21, FIG. 22, FIG. 23 and FIG. 24 illustrate another implant with endplate configuration, and processing operations for forming the same. Representatively, implant 302 and endplate coating 1422 are similar to the configuration described in FIG. 16-FIG. 20. In this aspect, however, masking members 2122 are further applied to form weak points or gaps 2422 between endplate coating 1422 and implant 302. The weak points or gaps 2422 can be used as starting points for breaking the endplate coating 1422 away from the cage. For example, the previously discussed revision surgery tool 308 can be inserted into the weak points or gaps 2422 to help the tool 308 pry the endplate coating 1422 away from implant 302. Representatively, as shown in FIG. 21, the endplate coating 1422 may be formed on implant 302 using nozzle 1420 as previously discussed. Masking members 2122, for example, in the form of strips, may then be formed over the endplate coating 1422. The masking members 2122 may be formed by applying strips of any suitable masking material that will prevent the endplate coating material from forming on the masked surface. In some aspects, the masking members 2122 are spaced apart from one another and formed entirely across the superior and/or inferior sides 302A, 302B of implant 302. In other aspects, each of masking members 2122 may be a series of discrete units that together form strips with gaps therein.

Representatively, in one aspect, masking members 2122 could be extruded onto the sides 302A-B using, for example, a ceramic or cement slurry, which could then have its liquid baked off, or dried out. In other aspects, masking members 2122 may be metallic strips that serve as a raft or support for coating 1722 to "float" on. In still further aspects, masking members 2122 could also be strips of allograft bone, DBF fibers, or high temperature plastic (such as PEEK), depending on the application temperature required for applying coating 1722. These layers could also be a resorbable material such that the connection between coating 1422 and coating 1722 could become weaker through the passing of time in anticipation of removing the implant in cases where the implant is temporary. Representatively, in one aspect the implant may be an implant fully of antibiotic beads that may need replacing with another implant once the first one has lost its effectiveness.

Figure 22:
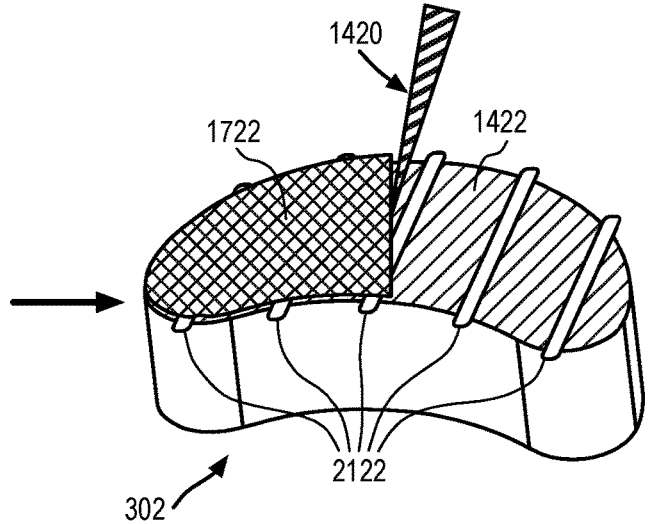
FIG. 22 shows a perspective view of another aspect of an interbody spinal implant.
Figure 23:
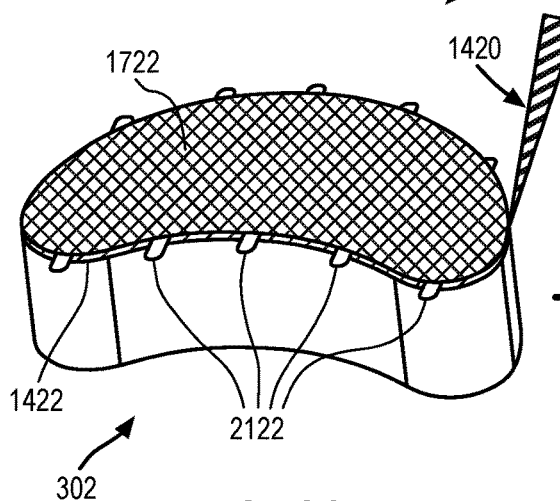
FIG. 23 shows a perspective view of another aspect of an interbody spinal implant.
Figure 24:
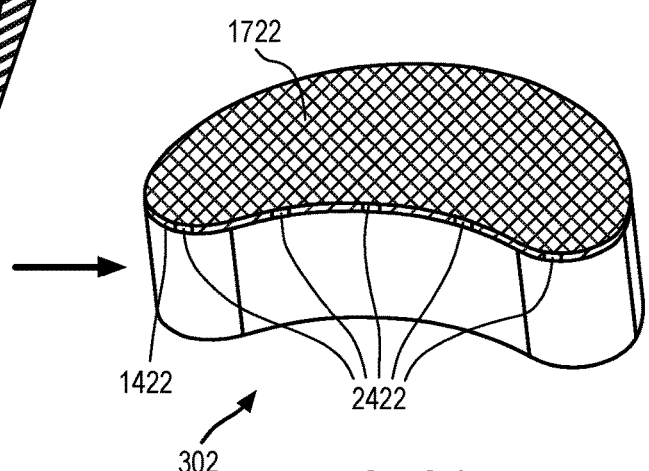
FIG. 24 shows a perspective view of another aspect of an interbody spinal implant.

As illustrated by FIG. 22, once masking members 2122 are formed, a second endplate coating 1722 may be applied over the endplate coating 1422 and masking members 2122. The second endplate coating 1722 may be applied entirely over the endplate coating 1422, as previously discussed in reference to FIGS. 17-18. In this aspect, the endplate coating 1422 and endplate coating 1722 with masking members 2122 formed in between are formed over the superior and/or inferior sides 302A, 302B of implant 302 as shown in FIG. 23. The masking members 2122 may then be removed by any suitable processing operation for removing masking material (without removing endplate coatings 1422, 1722). The removal of masking members 2122 results in the formation of weak points or gaps 2422 between endplate coating 1422 and endplate coating 1722. The weak points or gaps 2422 can be used by the tool 308 to separate the endplate coatings 1722 from endplate coating 1422 and, in turn, breakaway at least one of the coatings from implant 302 so implant 302 can be removed during revision surgery. For example, where the weak points or gaps 2422 are formed between endplate coatings 1422 and 1722, tool 308 is inserted into the gap 2422 and used to pry (or breakaway) endplate coating 1422 from endplate coating 1722. In this aspect, endplate coating 1422 remains attached to the implant 302 and endplate coating 1722 remains attached to the adjacent bone when implant 302 is removed. In other aspects, it is contemplated that the masking members 2122 may be formed directed on the superior or inferior sides 302A, 302B of implant 302, and then endplate coating 1422 and endplate coating 1722 are both formed over the masking members 2122. Upon removal of the masking members 2122 as previously discussed, the weak points or gaps 2422 are formed between the endplate coating 1422 and implant 302. In this aspect, the weak points or gaps 2422 may help to remove or breakaway the endplate coating 1422, along with the endplate coating 1722 formed over coating 1422, away from implant 302. Thus, when implant 302 is removed, endplate coating 1722 remains attached to the adjacent bone and endplate coating 1422 breaks away or otherwise decouples from implant 302. Upon insertion of a new implant 302, the new implant 302 may engage with the endplate coating 1422, 1722 remaining attached to the adjacent bone.

Figure 25:
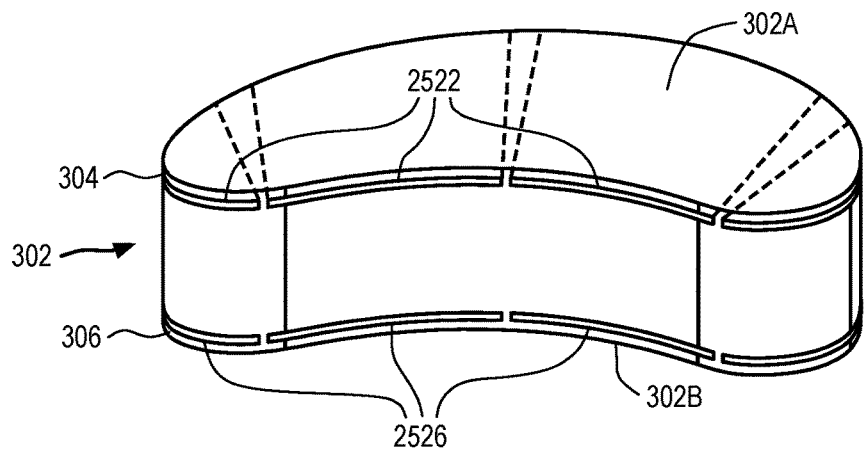
FIG. 25 shows a perspective view of another aspect of an interbody spinal implant.
Figure 26:
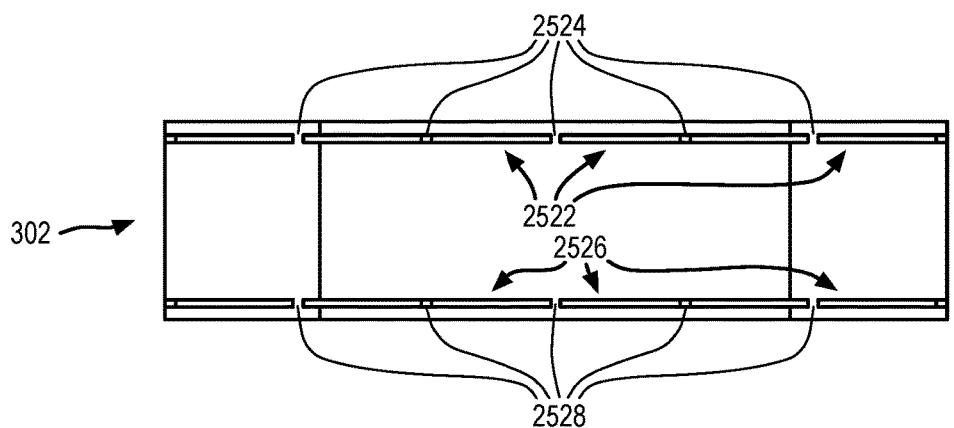
FIG. 26 shows a side view of another aspect of an interbody spinal implant.
Figure 27:
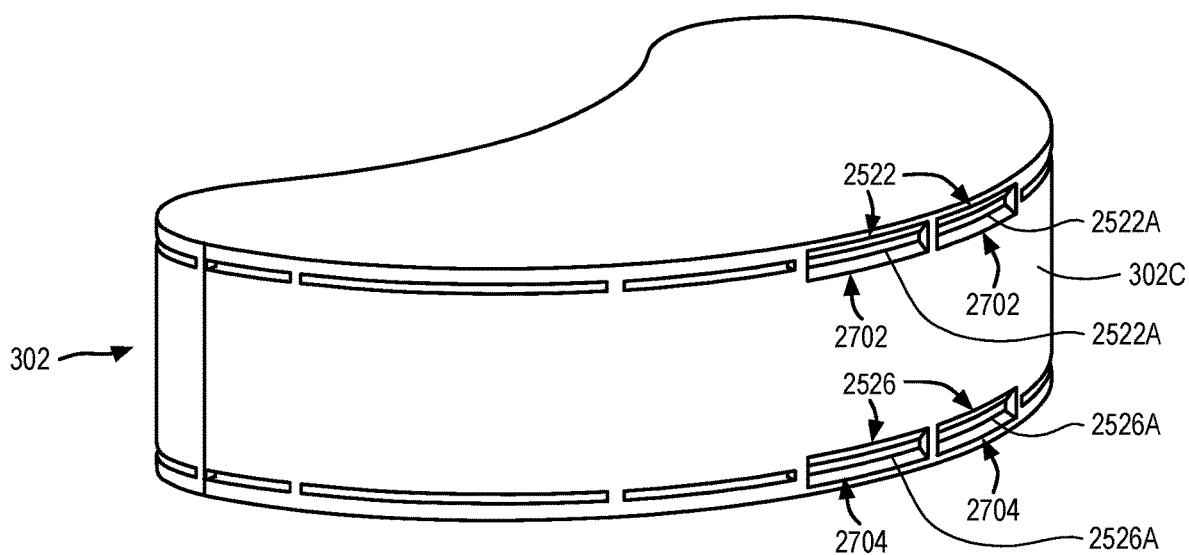
FIG. 27 shows a perspective view of another aspect of an interbody spinal implant.

FIG. 25, FIG. 26 and FIG. 27 illustrate another implant with endplate configuration, and processing operations for forming the same. Implant 302 having endplates 304, 306 may be similar to the previously discussed implants in which endplates 304, 306 are configured to breakaway or otherwise become decoupled from implant 302 to ease revision surgery. In this configuration, however, channels or slits 2522, 2526 are cut or formed into implant 302 to make the upper and lower most faces of implant (e.g., superior and inferior sides 302A, 302B) more easily loosened from the implant 302. Representatively, in some aspects, slits 2522, 2526 are formed through the anterior side to the posterior side of implant 302. Alternatively, slits 2522, 2526 are formed through the lateral sides of implant 302. Slits 2522, 2526 run in a direction parallel to the plane of the upper and lower most faces (e.g., the superior and inferior sides 302A, 302B). The slits 2522, 2526 form spaces between the upper most and lower most faces of implant 302 and the rest of the implant, and therefore effectively form endplates 304, 306. In some aspects, columns 2524, 2528 may remain between adjacent slits 2522, 2526 and/or within slits 2522, 2526 so that endplates 304, 306 can remain connected to the rest of implant 302 until it is desired to decouple the endplates 304, 306 from implant 302 during a revision surgery. In some aspects, the dimensions of columns 2524, 2526 may be tuned to provide more or less resistance to breakage. For example, in some aspects, one or more of columns 2524, 2528 may be wider to provide more resistance to breakage. In other aspects, one or more of columns 2524, 2528 may be narrower to provide less resistance to breakage. For example, thin columns (e.g, 0.3 millimeters or less) may provide little resistance to a surgeon using hand force, whereas thicker columns (e.g., 1 millimeter or more) may be extremely challenging to break, separate and/or divide by hand but could be accomplished with mechanical tools, possibly driven by motors/electricity, pneumatics or hydraulics, or cutting tools such as a saw or blade. In some aspects where thicker columns are used, notches may be formed in the columns which resist surgical and/or anatomic loading, but break easily when struck with a shearing loading.

Still further, one or more of columns 2524, 2528 may consist of a series of discrete column units extending across implant 302, and the number of discrete units may be selected to provide more or less resistance to breakage (e.g, more discrete column units increases resistance, less discrete column units decreases resistance). In some aspects, more or fewer columns 2524, 2528 may be used to provide more or less resistance to breakage. For example, more columns 2524, 2528 may be used to provide more resistance to breakage. In other aspects, less columns 2524, 2528 may be used to provide less resistance to breakage. During revision surgery, the tool (e.g., tool 308) may be inserted into one or more of slits 2522, 2526 and manipulated (e.g., moved up/down) to loosen and breakaway endplates 304, 306 from the rest of implant 302 without detaching endplates 304, 306 from the adjacent bone (e.g., vertebrae 102). The slits 2522, 2526 and columns 2524, 2528 may be formed by any suitable processing technique. For example, wire or plunge electrical discharge machining (EDM), a keyway cutter, sawing, water jet, acid or the like could be used to remove the thin slits of material leaving behind slits 2522, 2526 and columns 2524, 2528.

In addition, in still further aspects, slots or recessed regions 2702, 2704 could be formed at the end of slits 2522, 2526 as shown in FIG. 27. The recessed regions 2702, 2704 may serve as lead-ins to the slits 2522, 2526 that help to guide the tool used to breakaway the endplates 304, 306 into slits 2522, 2526. In this aspect, recessed regions 2702, 2704 may be similar in shape to the slit openings 2522A, 2526A, however, larger and in some cases have angled surfaces such that they essentially increase the size of the slit opening. In some aspects, recessed regions 2702, 2704 may entirely surround the slit openings 2522A, 2526A. In other aspects, recessed regions 2702, 2704 may be formed around fewer than all sides of the slit openings 2522A, 2526A. In addition, in some aspects, recessed regions 2702, 2704 may have angled edges that lead into the slit openings 2522A, 2526A to further help guide the tool into the slit opening 2522A, 2526A. Although shown positioned around only four slit openings 2522A, 2526A, recessed regions 2702, 2704 may be formed around any number of slit openings 2522A, 2526A.

While certain aspects have been described and shown in the accompanying drawings, it is to be understood that such aspects are merely illustrative of and not restrictive on the broad invention, and that the disclosure is not limited to the specific constructions and arrangements shown and described, since various other modifications may occur to those of ordinary skill in the art. For example, although in some aspects the endplates are shown as flat, they may be curved, uniconvex or bioconvex. In addition, one or more of the endplates may be at an angle to each other, such as lordotic (e.g., an angle opening to the front of the implant body) and/or kyphotic (e.g., an angle opening to the posterior of the implant body) to correct sagittal balance, or at an angle opening to the side to correct coronal imbalance. The description is thus to be regarded as illustrative instead of limiting. In addition, to aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What is claimed is:

1. An interbody spinal cage comprising:
   a body portion comprising a superior side, an inferior side and at least one lateral side connecting the superior side and the inferior side; and
   at least one endplate portion coupled to the superior side or the inferior side of the body portion, the at least one endplate portion comprising a unibody structure and operable to be fixedly coupled to an anatomical structure of a patient and decoupled from the superior side or the inferior side of the body portion, wherein at least one gap is formed between the endplate portion and the superior side or the inferior side while the body portion is fixedly coupled to the endplate portion, wherein the at least one gap facilitates decoupling of the endplate portion from the body portion.

2. The interbody spinal cage of claim 1 wherein the endplate portion is operable to be decoupled from the superior side or the inferior side upon application of a prying force between the endplate portion and the anatomical structure.

3. The interbody spinal cage of claim 1 wherein the endplate portion is coupled to the superior side or the inferior side by at least one fixation point near an anterior edge of the body portion.

4. The interbody spinal cage of claim 1 wherein the endplate portion is coupled to the superior side or the inferior side by a number of fixation points around a perimeter of the body portion.

5. The interbody spinal cage of claim 1 wherein the endplate portion comprises a coating formed on the superior side or the inferior side of the body portion.

6. The interbody spinal cage of claim 1 wherein the endplate portion comprises a number of material layers applied to the superior side or the inferior side of the body portion.

7. The interbody spinal cage of claim 1 wherein the endplate portion comprises a mesh.

8. The interbody spinal cage of claim 1 wherein at least one slot leading into the at least one gap is formed in the body portion.

9. An interbody spinal implant comprising:

a body portion comprising a superior side, an inferior side and at least one lateral side connecting the superior side and the inferior side; and at least one endplate coating, the at least one endplate coating operable to be fixedly coupled to an anatomical structure of a patient and decoupled from the body portion, wherein the endplate coating comprises a first layer of endplate material formed on the superior side or the inferior side of the body portion, and a second layer of endplate material formed on the first layer of endplate material, and wherein the second layer of endplate material remains fixedly coupled to the anatomical structure and is operable to be decoupled from the first layer of endplate material to decouple the endplate coating from the body portion.

10. The interbody spinal implant of claim 9 wherein the endplate coating comprises a single layer of endplate material formed on the superior side and the inferior side of the body portion.

11. The interbody spinal cage of claim 1 wherein the at least one gap runs along the at least one lateral side.

12. The interbody spinal cage of claim 1 wherein the at least one gap extends from the inferior side to the superior side.

* * * * *